United States Patent [19]

Schindler et al.

[11] Patent Number: 4,486,291
[45] Date of Patent: Dec. 4, 1984

[54] MEASURING APPARATUS FOR THE DETERMINATION OF OXYGEN PARTIAL PRESSURE IN FLUIDS AND GASES

[75] Inventors: Johannes G. Schindler; Maria Schindler nee Kardosova, both of Marburg an der Lahn, Fed. Rep. of Germany

[73] Assignee: Fresenius AG, Fed. Rep. of Germany

[21] Appl. No.: 415,277

[22] Filed: Sep. 7, 1982

Related U.S. Application Data

[63] Continuation-in-part of Ser. No. 170,556, Jul. 21, 1980, abandoned.

[51] Int. Cl.³ .................. G01N 27/30; G01N 27/54
[52] U.S. Cl. ............................................. 204/415
[58] Field of Search .......................... 204/415; 128/635

[56] References Cited

U.S. PATENT DOCUMENTS 3,957,607  5/1976  Simon ............................... 204/180 P
4,263,115  4/1981  Kessler et al. .................... 204/415 X

OTHER PUBLICATIONS

Konrad Dorfner, "Ion Exchangers, Properties and Applications", pp. 16–26, (1973).

Primary Examiner—G. L. Kaplan
Attorney, Agent, or Firm—Omri M. Behr

[57] ABSTRACT

There is provided a measuring apparatus for determination of oxygen partial pressure in liquids and gases which comprises a substantially sheathed metallic cathode having a small, unsheathed metallic surface and a metallic anode, an ion impermeable but gas permeable membrane interposed between the material whose oxygen content is to be measured and the unsheathed metallic surface of the cathode, an electrolyte between said cathode and said anode and a barrier layer impermeable to cations of the material forming the anode, interposed between said anode and said unsheathed metallic surface of said cathode. Preferably said metallic anode is a silver anode enveloped with silver chloride being covered with said barrier layer.

6 Claims, 3 Drawing Figures

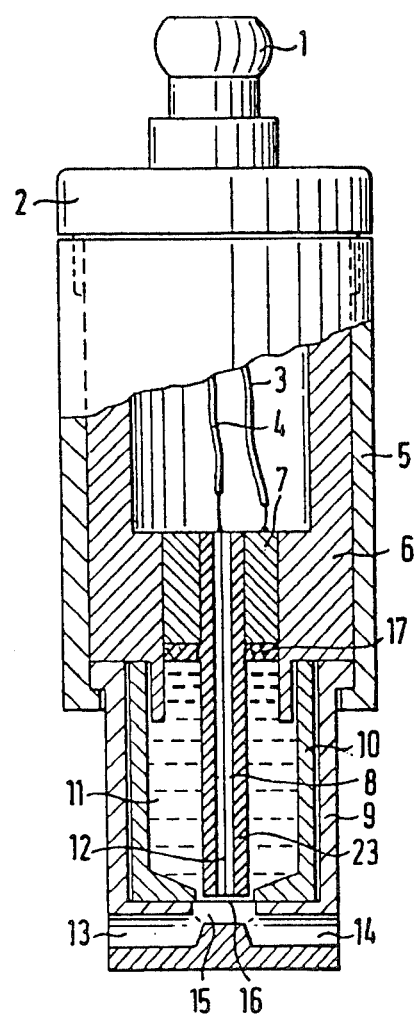
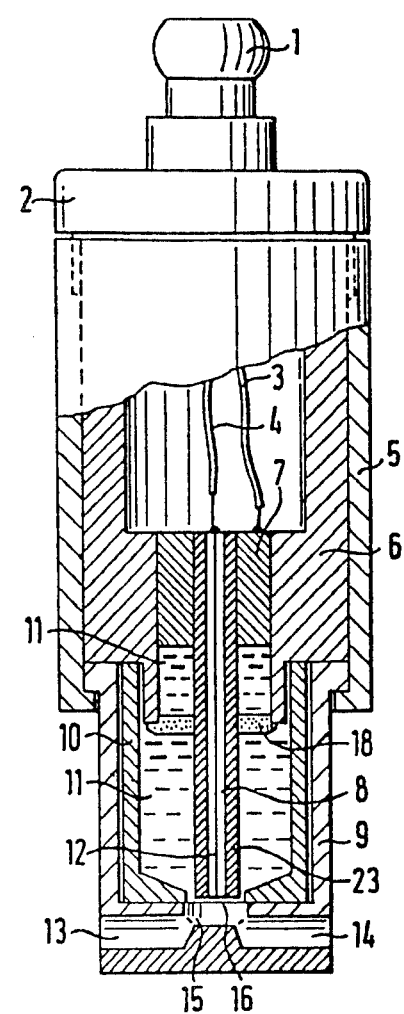

MEASURING APPARATUS FOR THE DETERMINATION OF OXYGEN PARTIAL PRESSURE IN FLUIDS AND GASES

This application is a continuation-in-part of application Ser. No. 170,556, filed July 21, 1980 and now abandoned.

BACKGROUND OF THE INVENTION

The invention concerns a measuring apparatus or probe for continous determination of oxygen partial pressure in liquid and in gases particularly in blood. The measurement of oxygen partial pressure is carried out with the aid of gas-sensitive electrodes and in particular by the determination of the reduction current which flows as a result of the attachment of the oxygen to the cathode as soon as a potential source is applied between the cathode and the anode and the two electrodes are in communication with each other via an electrolyte. Although the course of the reaction is still not fully understood, one may assume that the oxygen which is present at the electrode is reduced there by the attachment thereto of electrons and, in accordance with the following equation, is converted into hydroxyl ions.

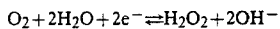

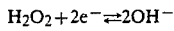

At the anode a portion of the atoms of the anode material is oxidized to ions which is equivalent to the electron surrender at the cathode, thus in the case of the silver anode, silver atoms are converted to silver ions ($Ag^+$). The thus flowing current is dependent upon the number of oxygen molecules which arrive at the cathodic surface. Where the potential difference between the anode and the cathode is sufficiently large to reduce all oxygen molecules which arrive at the cathode, then in the inner portion of the plateau of the polarogram even a raising of the potential will not bring about an increase in the current. That is to say that the current flow is then independent of the applied potential and is only determined by the number of oxygen atoms which arrive at the cathode. This current provides a quantitative standard for the determination of the oxygen partial pressure present in the test solution.

In order to carry out the measurement of the oxygen partial pressure heretofore it has been preferred to use measuring arrangements with a glass enveloped cathode made of platinum or other noble metals which is separated from the measuring chamber, in which the test sample is to be found, by a membrane which is impermeable to ions but is permeable to oxygen. The measuring probe itself for example, comprises a glass enveloped platinum electrode, whose tip is freely accessible in the end surface of the glass envelope. Silver electrodes are the most frequently used as the anode which, in order to increase the stability of the readings therefrom, may be coated with a layer of silver chloride. Anodes and cathode tips are surrounded and connected by a solution of electrolytes, suitably a 0.2 molar solution of potassium chloride.

The aforementioned separation of the test material from the measuring sensor has the purpose of preventing changes in the electrodes due to precipitation, for example by reducing or oxygenating substances present in the test material. The exactness of the measurement is, however, also influenced by an observed instability of the measuring probe itself. Research in this area has shown that the determination of the oxygen partial pressure by measurement of the current flow between a cathode and an anode is falsified by a superimposed current which, to a substantial extent, occurs as the result of the migration of ions of the anode material, for example the silver ions to the cathode. This so called silver ion drift also occurs when the anode is covered with a silver chloride layer since experience has shown that such a coating contains certain gaps through which the silver ions may pass. As one has seen through microscopic examination of the free cathodic surface, it has not been possible to prevent the contamination of the free cathodic surface by the migration of silver ions, such contamination becomes worse with time of use of the device. These changes in the free cathodic surface are the principle cause of the measuring instability of the measuring probe and a source of error in the determination of oxygen partial pressure.

It would be desirable therefore, to provide a measuring device for the continuous determination of oxygen partial pressure in fluids and gases, in particular in blood, whose measuring value stability vis a vis the known measuring devices is improved so that the measuring arrangement may be used for a longer operating period of time without the need for interrupting the measurement to clean the cathode.

SUMMARY OF THE INVENTION

In the apparatus of the present invention there is provided a measuring device wherein the cathode need not be removed for cleaning. The novel apparatus comprises a cathode eventually enveloped by a suitable isolating material for example glass having a small unsheathed surface and a metal anode, suitably enveloped with silver chloride, both of which are in communication via an electrolyte. A blocking layer which is impermeable to the cations of the anode material is located between the anode and the cathode.

A membrane, impermeable to liquids and ions, but permeable to oxygen is provided proximate to the unsheathed portion of the cathode. This membrane may be placed directly on the said exposed portion, being part of a housing surrounding the anode and the cathode, said housing having an opening proximate the aforesaid exposed portion which is closed with said oxygen permeable membrane.

Through the avoidance of the deposition on the free cathodic surface of anodic materials which had been converted into the ionic condition and dissolved in the electrolyte it is possible to measure the partial pressure of oxygen in an error-free manner. It is thus possible to increase the stability of measurement of the arrangement by a substantial multiple. It has been determined experimentally that this factor is between 10 and 100.

It is therefore now possible with the aid of the measuring apparatus of the present invention to carry out experiments and series of measurement over a longer period of time without the need to interrupt the work through repeated disassembly of the measuring arrangement for cleaning the cathode, which necessitates repeated recalibration of the apparatus in order to determine the apparatus constants.

The possibility of carrying out measurements over longer periods of time makes entirely new uses available for the herein described measuring method. For example, it is now possible to insert measuring arrangements of the novel type into the human body in the form of probes for the determination and monitoring of oxygen partial pressure. The measuring arrangement may be employed as a monitor for extended time measurements such as artifical respiration, monitoring of enzymic processes such as glucose consumption, monitoring of oxygen supply in combustion processes as well as in fermentation processes.

The avoidance of ionic transfer from the anode to the cathode is achieved by the provision of a barrier layer of cation blocking substances. These substances may be organic or inorganic anion exchangers.

All of the foregoing substances can be found in a matrix, that is to say, immobilized by binding to or incorporation into polymeric substances.

The apparatus formed in accordance with the present invention can be utilized as an immersion electrode, as a catheter electrode, as a flowthrough electrode, or as an incision electrode. It can also be used as a secondary electrode in a system provided with enzyme membrane, for example, for the determination of glucose. Individual aspects of the invention will appear from the hereinbelow described experiments.

These experiments were carried out by use of measuring arrangements which are set forth in the drawings and which are described in detail hereinbelow.

Basically, however, it is foreseen that the invention should be used with measuring arrangements or measuring probes of other construction with the proviso that the electrolyte volume in which the anode and the cathode are held are separated from the material to be measured by an ion impermeable but oxygen permeable membrane.

In the descriptions of the present invention the combination of a silver anode and platinum cathode is preferred, however, the invention should not be considered as limited thereto. However, where other combinations of anodic and cathodic materials are used, the same purpose is served by the anodic ion barrier.

BRIEF DESCRIPTION OF THE DRAWINGS

FIG. 1 is an elevational cross-sectional view of an apparatus in the form of a measuring probe whose anode is covered with a blocking layer, according to the principles of the present invention;

FIG. 2 is an elevational cross-sectional view of a measuring probe whose electrodes are separated from each other by a blocking layer provided in the space between them.

DESCRIPTION OF THE PREFERRED EMBODIMENTS

Figure 3:
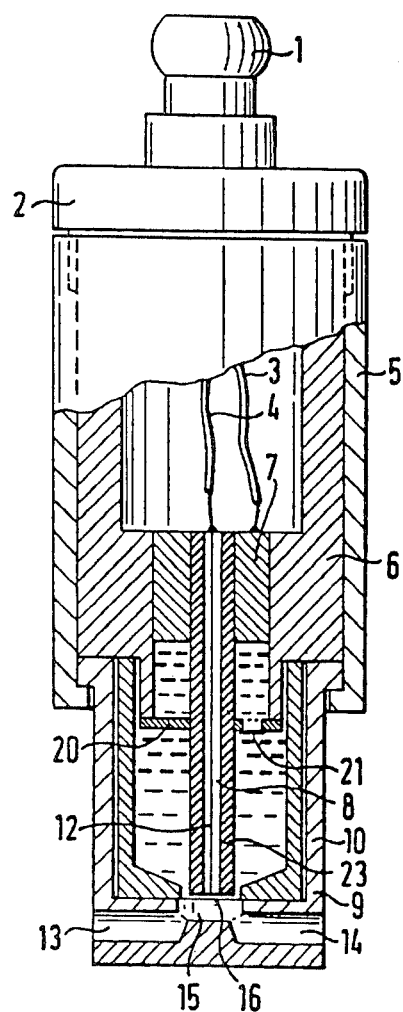
FIG. 3 is an elevational cross-sectional view of a measuring probe wherein a barrier closed by a membrane is provided between both electrodes.

As illustrated in the elevational cross-section shown in FIG. 1 there is provided a contact plug 1 which is affixed to electrode head 2. The electrode holder or container 6 for carrying the electrode arrangement is constructed of insulating material and is connected with the electrode head 2. The electrode arrangement comprises a platinum cathode 12 and a silver anode 7. One end of the platinum cathode 12 is welded to its lead 4, also of platinum, and the other end thereof is enveloped in a bonded glass sheath 8, approximately 1 mm in thickness. The glass sheath 8 is itself surrounded by an insulating sheath 23 and, partially, by silver anode 7. It should be noted that a substantial proportion of the forward end of the cathode sheath 23 protrudes from anode 7. The tip of platinum cathode 12 which suitably has a diameter of about 15 um is freely accessible in the forward portion of the glass sheath 8. The contact wire 3, one end of which is attached to anode 7 is connected with plug 1. A blocking layer (in FIG. 1, number 17, in FIG. 2, number 18, in FIG. 3, number 21) is provided between the anode and the unsheathed portion of the cathode.

The combination of platinum cathode 12 and the silver electrode 7 in the electrode housing formed from plug 1 electrode head 2 is surrounded by electrode container 6. A cylindrical housing tent 10 of insulating material suitably polytetrafluroethylene surrounds the lower end of the electrode arrangement 7 and 12 and contacts the bottom of holder 6. The inner portion 11 of the housing 10 provides the space for electrolyte of the measuring cell. Suitably this space is filled with unbuffered electrolyte, suitably 0.1 to 0.2 molar potassium chloride. Onto the forward surface of housing 10 is sealed an oxygen permeable membrane 16, suitably of polytetrafluroethylene. The membrane 16 has a thickness of between 5 and 50 m$\mu$ suitably about 12 m$\mu$. The length of the housing 10 is desirably so chosen that membrane 16 contacts the head portion of platinum cathode 12 whereby a very thin electrolyte film remains between the cathode and the membrane.

A measuring chamber housing 9 surrounds housing 10. This outer housing is made of an insulating polymeric material suitably polyacrylic glass and is provided with a flange so that the whole construction can be held together with a surrounding nut 5 attached to electrode head 2. A measuring chamber 15 is provided in measuring chamber housing 9 having one wall open, said one wall will be formed by membrane 16 when being assembled. The measuring chamber 15 is provided with inflow and outflow passages 13 and 14 and has a volume of approximately 1 microliter.

FIG. 2 shows a further embodiment of a measuring probe which is still substantially similar to the probe of FIG. 1. In this embodiment however in place of layer 17 an annular blocking disc 18 is provided in the space between the electrodes and there forms a barrier through which silver ions cannot pass. The barrier disc 18 is for example made of a sponge-like polymeric matrix having absorbed therein an anion exchanger of the type set forth hereinbelow. The outer edge of barrier disc 18 is sealably attached to the electrode holder 6 and the inner surface of disc 18 to outer wall surface of glass sheath 8 or more suitably its surrounding insulating sheath 23.

In the embodiment of the present invention shown in FIG. 3 the electrolyte-filled measuring chamber is interrupted by an obstructing disc 20 which may, suitably, be made of an impermeable synthetic material. In this wall there is provided an opening which is sealed by a membrane 21. This membrane comprises a polymeric matrix having an anionic ion exchanger integrated therein. The barrier disc 20 and the membrane 21 are both impermeable to silver ion entering the solution from the anode.

The anode in all of the foregoing embodiments is covered with a silver chloride layer 22. At this stage it should be noted here that the provision of a blocking layer 17 or a membrane 18 or 21 does not alter the determination of oxygen partial pressure. The only influence that may be noted from the provision of a barrier layer upon the outer surface of the cathode can be a lengthening of the diffusion time of the oxygen.

This does not, however alter the absolute value measured therefor.

Generally speaking, it is preferred, in accordance with the invention, to place the blocking layer (17, 18, or 21) on the outer surface of the electrode which comes in contact with the electrolyte wherein, similarly, this can already have been coated with silver chloride.

If the substance forming blocking layer in question has a solid or highly viscous consistency at room temperature, then it is preferred to dissolve this material in an organic solvent which is then painted or sprayed onto the electrode. This procedure, after drying, is then repeated several times until a layer thickness of between 0.1-1.0 mm suitably 0.5 mm to 0.7 mm is achieved. It has also been determined to be advantageous when the layer forming substance is a solid at room temperature to mix this substance with a polymer or to bring both into the liquid state whereby an ion selective polymer is formed. The advantage of such a proceeding is found therein that thereby there is formed a particularly dense, stable, and long-lived blocking material with particularly good adhesion power. Suitable ion exchangers and complex formers may themselves be formed by the polymerization process.

If the desired blocking substance is liquid at room temperature then it is advantageous to combine it with a polymer or to incorporate it into a polymeric matrix. Equally the blocking substance may be formed by saturating a carrier with a material which will block the passage therethrough of anions of the anodic material. As carrier materials there may be utilized porous material, felts, foams, and the like which are placed between the anode and the cathode. They can also be placed as membranes between the two electrodes.

A further possibility exists in the provision of a blocking layer which may be coated upon the portion of the cathode protruding from the glass sheath, it is also possible to combine it with isolating sheaths surrounding the glass sheaths.

Hereinbelow there will be listed certain of such substances which may be utilized for the blocking layer of the present invention. It should be noted that this list is not limiting but may be amplified by anyone skilled in the art.

In the category of organic ion exchangers there may be listed anionic exchangers substances which are insoluble in water but are soluble in water-immiscible organic solvents suitably synthetic resins, aliphatic and/or aromatic, primary, secondary, and tertiary amines and/or quaternary ammonium bases. Useful in this category are polyelectrolytes of the so-called caterpillar category and anionic exchangers of the pyridine type. As liquid anion exchangers there may be set forth: Tri-n-octylamine, Tri-iso-octylamine, Tri-2-ethylhexylamine, Tribenzylamine, Didecylamine, Methyldioctylamine, Methyldidecylamine, Tridodecylamine, Tributylamine.

Residual amine mixtures are commercially available. For example, trialkylmethylamine (a mixture of homologs with 18-24 carbon atoms commercially known as Primene JM N-Dodecenyl-N-trialkyl-methylamine (mixture of homologs with 24-27 carbon atoms) Amberlite LA-1 manufactured by Röhm and Haas Co.; N-Lauryl-N-trialkyl-methylamine Amberlite LA-2); N,N-Didodecenyl-N-n-butylamine (Amberlite XE 204) or manufactured by Röhm and Haas; Tricaprylamine; Trioctylmethyl ammonimum chloride (Aliquat 336 S, manufactured by General Mill Comp. or Adogen 464 manufactured by Serva) or Dimethyldistearyl ammonium chloride.

The ligands can be charged and/or neutral and may be single and/or multitoothed. Charged and uncharged ligands may work selectively with respect to anions.

As examples of charged ligands there may be mentioned liquid anion exchangers such as trioctylmethyl ammonium chloride and dimethyldistearyl ammonium chloride.

All of the foregoing materials may be used, as mentioned herein, either per se or bound in or to polymeric materials. For example, in a lipophilic membrane phase or in a polymeric matrix comprising, for example, polyvinylchloride, a suitable plasticizer, such as tris (2) ethylhexyl (phosphate) or dinonylphalate and the appropriate lipophilic ligand mentioned above.

See also a listing of neutral anion selective macrotricyclic ligands disclosed by Metz, et al, J.S.C., Chem. Comm. 533, (1976). The disclosures of the foregoing references are incorporated herein by reference.

EXAMPLE 1

Preparation of Blocking Layer

The blocking layer 17 is formed in the following manner. (a) A solution of polyvinyl chloride in cyclohexanone (gml, 15% w/w) and trioctylmethylammonium chloride (1.5 ml) is prepared and layered several times upon the anode of FIG. 1. Each layer is permitted to dry for about 5 hours at ambient temperature between 2 and 5 layers are suitably applied until the total thickness is approximately 0.5 mm to 0.7 mm.

(b) Similarly, but utilizing a solution of polyvinyl chloride is cyclohexanone (10 ml, 15% w/w) together with 1 ml dimethylstearyl ammonium chloride, the mixture is similarly layered, similarly dried at room temperature from 2-5 suitably 5 times to provide a thickness of between 0.5 and 1.5 suitably 1 mm.

In accordance with the above procedure, but where in place of dimethyl stearyl ammonium chloride there is utilized any of the other amines, quaternary ammonium bases or polyelectrolytes ion exchangers as active components of the aniodic ion blocking layer, a similar product is attained.

EXAMPLE 2

The anode is not coated with a silver chloride layer and there is no barrier layer between the anode and the cathode.

EXAMPLE 3

The measuring probe utilizes a silver chloride covered anode however there is no silver ion impermeable barrier layer provided.

EXAMPLE 4

A barrier layer comprising an ion exchanger layer 17 is located upon anode 7. This barrier layer is of the type illustrated in FIG. 1, and prepared according to Example 1a.

EXAMPLE 5

The device utilized is constructed in accordance with Example 4 additionally however a silver chloride layer is interposed between the barrier layer 17 and the silver anode 7.

The general conditions of the experiment are the same in all four examples, the cathode of the measuring probes comprises a platinum wire of approximately 15 μm, the electrolyte is a potassium chloride solution in the range of 0.1 mole per liter through 1 mole per liter.

Calibration experiments were carried out in the absence of oxygen. The experiments of Examples 2 and 3 were found unsatisfactory at this stage.

In Example 2 it was found that the null current value rises rapidly so that after only three days running time the measuring probes must be abandoned as useless.

In Example 3, namely that having a silver-chloride coated anode, the value of the current rises approximately 0.03 nA per day. The measuring probe was designated as useless after four weeks on grounds of too high a null current and a clear loss of stability.

Experiments to determine the oxygen partial pressure in an atmosphere saturated with water vapor were carried out over extended periods of time with measuring probe prepared in accordance with Examples 4 and 5. In these experiments approximately 60 ml of air per hour pass through the measuring chamber of the probes. The resultant measurements utilizing these measuring arrangements in accordance with the invention remain reproducible within a range of error of ±0.01 nA. The experiments were terminated after three months without any appearance of aging in the probes. The free cathode surface, after microscopic examination shows no change.

The measurement results which were obtained from a measuring probe of Example 3 wherein the anode is only coated with the silver chloride layer (i.e. no silver ion impermeable barrier) show, in the same time span, a value change of approximately 100%. A substantial rise in the measured current is noted with an increased null current. The measuring probe demonstrates an instability which increases with time.

It may further be mentioned that when the test gas is changed from pure nitrogen to pure oxygen an electrode prepared in accordance with present invention reaches 99.8% of its final value within 10 to 15 seconds.

The experimental results show that a constant stability over a long time span may be achieved by utilizing electrodes in accordance with the present invention. In other words the effective use time is substantially increased.

Having thus set forth the nature of the invention what is claimed is:

1. Measuring apparatus or probe for the determination of oxygen partial pressure in liquids and gases comprising:
    (a) a metallic cathode substantially sheathed by an insulating material having a small unsheathed metallic surface,
    (b) an anode,
    (c) a barrier layer impermeable to cations of the material forming the anode comprising at least one member selected from the group consisting of organic or inorganic anion exchangers and interposed between said anode and said unsheathed metallic surface of said cathode, and
    (d) a liquid impermeable, ion impermeable but gas permeable membrane interposed between the material whose oxygen content is to be measured and the unsheathed metallic surface of the cathode.

2. A measuring apparatus in accordance with claim 1 further comprising a liquid electrolyte.

3. A measuring apparatus in accordance with claim 2 further including: a housing substantially enclosing said anode, said barrier layer and said cathode, said housing including:
    (i) an insulating impermeable major portion, and
    (ii) a minor portion located proximate to the unsheathed portion of the cathode said minor portion being impermeable to liquids but permeable to gases.

4. An apparatus in accordance with claim 3 said electrolyte being provided in said housing between said barrier layer and said unsheathed portion of said cathode, said minor portion being disposed to provide the presence of a thin film of electrolyte between it and the unsheathed portion of the cathode.

5. An apparatus in accordance with claim 2 further including a silver chloride layer placed upon the outer surface of the anode.

6. An apparatus in accordance with claim 1 further including a silver chloride layer placed upon the outer surface of the anode.

* * * * *

UNITED STATES PATENT AND TRADEMARK OFFICE
CERTIFICATE OF CORRECTION

PATENT NO. : 4,486,291

DATED : December 4, 1984

INVENTOR(S) : Johannes G. Schindler, Maria Schindler nee Kardosova

It is certified that error appears in the above-identified patent and that said Letters Patent are hereby corrected as shown below:

On the title page add:

[30] Foreign Application Priority Data

July 25, 1979 [DE] Fed. Rep. Germany 29 30 074

Signed and Sealed this

Twenty-first Day of May 1985

[SEAL]

Attest:

DONALD J. QUIGG

Attesting Officer     Acting Commissioner of Patents and Trademarks